US009168256B2

(12) United States Patent
Faruqui et al.

(10) Patent No.: US 9,168,256 B2
(45) Date of Patent: Oct. 27, 2015

(54) STABLE SOLID DOSAGE FORMS OF AMINOPTERIN

(75) Inventors: Absar Faruqui, Auburn, WA (US); John A. Zebala, Sammamish, WA (US); Barton A. Kamen, Princeton Junction, NJ (US)

(73) Assignee: Aminopterin LLC, Auburn, WA (US)

( * ) Notice: Subject to any disclaimer, the term of this patent is extended or adjusted under 35 U.S.C. 154(b) by 1467 days.

(21) Appl. No.: 11/928,257

(22) Filed: Oct. 30, 2007

(65) Prior Publication Data

US 2008/0058338 A1 Mar. 6, 2008

Related U.S. Application Data

(63) Continuation-in-part of application No. 11/078,614, filed on Mar. 9, 2005, now Pat. No. 7,612,071.

(60) Provisional application No. 60/552,787, filed on Mar. 12, 2004.

(51) Int. Cl.
*A61K 31/519* (2006.01)

(52) U.S. Cl.
CPC .................................... *A61K 31/519* (2013.01)

(58) Field of Classification Search
CPC .................................................... A61K 31/519
See application file for complete search history.

(56) References Cited

U.S. PATENT DOCUMENTS

| | | | | |
|---|---|---|---|---|
| 2,443,165 | A | 10/1946 | Hultquist et al. | |
| 2,575,168 | A | 7/1948 | Franklin | |
| 4,077,957 | A | 3/1978 | Piper et al. | |
| 4,079,056 | A | 3/1978 | Piper et al. | |
| 4,401,592 | A * | 8/1983 | Yoshikumi et al. | 424/181.1 |
| 5,516,531 | A * | 5/1996 | Makino et al. | 424/494 |
| 6,197,787 | B1 * | 3/2001 | Franson et al. | 514/313 |
| 7,235,660 | B1 | 6/2007 | Zebala et al. | |
| 2002/0147208 | A1 * | 10/2002 | Fleshner-Barak et al. | 514/283 |
| 2010/0009998 | A1 * | 1/2010 | Kamen et al. | 514/249 |
| 2010/0190798 | A1 * | 7/2010 | Zebala et al. | 514/249 |

FOREIGN PATENT DOCUMENTS

| | | | |
|---|---|---|---|
| GB | 1107632 | A | 3/1968 |

OTHER PUBLICATIONS

Sidney Farber, et al, Advances in Chemotherapy of Cancer in Man, in Advances in Cancer Research 1 (Jesse Greenstein & Alexander Haddow, eds. 1956).*
Gubner et al. J. Med. Sci. 221:169-175, 1951.
Gubner et al. Arch. Derfmatol. Syphilol. 64:688-699, 1951.
Ratliff et al.; "Phase I and Pharmacokinetic Trial of Aminopterin in Patients with Refractory Malignancies"; Journal of Clinical Oncology; vol. 16 No. 4; Apr. 1998; p. 1458-1464.
Gubner; "Therapeutic Suppression of Tissue Reactivity: I. Comparison of the Effects of Cortisone and Aminopterin"; American Journal of the Medical Sciences; vol. 221 No. 2; Feb. 1951; p. 169-175.
Gubner; "Effect of Aminopterin on Epithelial Tissues"; A.M.A. Arch. Derm. Syphilol; vol. 64 No. 6; Dec. 1951; p. 688-699.
Rees et al., Arch. Dermatol. 90:544-52, 1964.
Cole et al., Clin. Cancer Res. 11(21):2005.
Gubner, R., Am. J. Med. Sci. 221(2):169-175. Feb. 1951.
Gubner, R., Am. J. Med. Sci. 221(2):176-182, Feb. 1951.
Gubner, R. Ama Arch. Dermatol. Syphilol. 64(6):688-699. Dec. 1951.
Burchenal, J., et al., Cancer. 2:113-118. 1949.
Dacie J., et al., Aminopterin in the treatment of acute leukaemia. B.M.J. 1:1447-1457.
Farber, S., et al., Advances in cancer research, pp. 2-73. New York Academic Press, New York, NY. 1956.
Glode, M., et al., Can. Res. 39:3707-3714. 1979.
Goldin, A., et al., J. Natl. Cancer Inst. 5:5425-5426. 1953.
Heinrich, M., et al., J. Am. Chem. 75:5425-5426. 1953.
Hutchinson, J., et al., Proc. Am. Assoc. Cancer Res. 1:26, 1953.
Loo, T. J. Med. Chem. 8:139. 1965.
Oliverio, V. Anal. Chem. 33(2):263-265. 1961.
Sacks, M., et al., Ann. Intern. Med. 32:80-115. 1950.
Seeger, D., et al., J. Am. Chem. Soc. 71:1753-1758. 1949.
Seeger, D., et al., J. Am. Chem. Soc. 69:2567. 1947.
Sirotnak, F., & Donsbach, R. Biochem. Pharmacol. 24:156-158. 1975.
Waller, C., et al., J. Am. Chem. Soc. 70:19-22. 1948.
Weygand, F., et al., Z. Naturforsch. 6b:174. 1951.

* cited by examiner

*Primary Examiner* — Sean Basquill
(74) *Attorney, Agent, or Firm* — Baker & Hostetler LLP

(57) ABSTRACT

There is disclosed stable pharmaceutical compositions containing pharmaceutically acceptable salts of aminopterin surface deposited onto solid excipients. The stable pharmaceutical compositions are hermetically sealed from the atmosphere. The formation of degradation products of aminopterin is reduced or eliminated.

13 Claims, No Drawings

STABLE SOLID DOSAGE FORMS OF AMINOPTERIN

The application is a continuation-in-part of pending U.S. patent application Ser. No. 11/078,614 filed 9 Mar. 2005, the teachings of which are incorporated herein by reference for all purposes, which claims the benefit of U.S. Provisional Patent application No. 60/552,787, filed 12 Mar. 2004.

TECHNICAL FIELD

The disclosure relates to stable pharmaceutical compositions containing pharmaceutically acceptable salts of aminopterin surface deposited onto solid recipients or hermetically sealed from the atmosphere, wherein the formation of degradation products has been reduced or eliminated.

BACKGROUND

Aminopterin, or N-4-[[2,4-diamino-6-pteridinyl)-methyl] amino]benzoy-1]-L-glutamic acid, is a potent antifolate useful for treating a variety of human diseases. Rees et al. noted in 1964 that aminopterin instability was a problem in the tablet previously produced and marketed by Lederle Laboratories [Rees et al., *Arch. Dermatol.* 90:544-52, 1964]. Cole noted that liquid dosage forms degraded to folic acid over time [Cole et al., *Clin. Cancer Res.* 11(21):2005].

The therapeutic index of aminopterin is very narrow, and therefore accurate dosing is essential to achieve optimum efficacy and avoid harmful side-effects and potential lethality. Unstable dosage forms lead to inaccurate dosing, and risk to the patient.

SUMMARY

The present disclosure provides a stable pharmaceutical composition comprising a pharmaceutically acceptable salt of aminopterin surface deposited onto solid excipients by a wet granulation process. Preferably, the stable pharmaceutical composition is hermetically sealed from the atmosphere. The disclosed stable pharmaceutical composition prevents or significantly reduces the formation of aminopterin degradation products.

The present disclosure provides a stable pharmaceutical composition having an aminopterin salt deposited on the surface of an excipient, comprising a plurality of granules having a solid body and a surface, wherein each granule comprises one or a mixture of excipients to and wherein the aminopterin salt is dried onto the surface of the granule. Preferably, the aminopterin salt is aminopterin disodium. Preferably, the aminopterin salt is from about 0.01 weight percent to about 10 weight percent of each granule, more preferably from about 0.1 weight percent to about 1 weight percent of each granule, and most preferably from about 0.25 weight percent to about 1 weight percent of each granule. Preferably, the total amount of aminopterin salt is in each dose is from 0.01 mg to 4 mg, and wherein each dose comprises a plurality of granules. Preferably, the excipient is a plurality of different excipients, wherein each member of the plurality of excipients is selected from the group consisting of surfactants, diluents, binders, amino acids, solubilizers, disintegrants, fillers, lubricants, buffers, stabilizers, colorants, dyes, anti-oxidants, anti-adherents, preservatives and glidants.

The present disclosure further provides that the stable pharmaceutical composition comprising a plurality of granules is hermetically sealed from the atmosphere.

According to another aspect, the disclosure provides a method for preparing a stable pharmaceutical composition comprising about 0.01 wt. % to about 10 wt. % of an aminopterin salt, and about 90 wt. % to about 99.99 wt. % of one or a plurality of excipients, wherein the formation of degradation products has been reduced or eliminated, and the weight percents are based on the total weight of the pharmaceutical composition. Preferably, the method for preparing a stable pharmaceutical composition of aminopterin salt comprises: (a) mixing the aminopterin salt and a solvent, to form a solution; (b) adding the solution to one or more excipients to form a wet granulation; (c) drying the wet granulation to form granules, and optionally milling the granules; and (d) optionally mixing one or more excipients with the granules to form a pharmaceutical composition.

The stabilized pharmaceutical compositions of aminopterin exhibited a number of commercial advantages including: (i) the aminopterin salt present in the compositions was preserved from degradation; (ii) the disclosed compositions exhibited extended shelf-life under normal storage conditions; (iii) the effect of moisture on the pharmaceutical compositions was minimized; and (v) the pharmaceutical compositions exhibited minimal, if any, instability, permitting highly accurate and known dosing.

DETAILED DESCRIPTION

The stable pharmaceutical compositions of the disclosure contain a pharmaceutically acceptable salt of aminopterin surface deposited onto solid excipients by a wet granulation process, or are hermetically sealed from the environment. It has been unexpectedly found that solid salts of aminopterin are highly hygroscopic in the atmosphere, forming no fixed hydrate stoichiometry, but instead continuing to adsorb moisture. Without being bound by theory, it is believed that aminopterin salts that are surface deposited onto a relatively large excess of solid excipients as disclosed herein, are no longer in a molecular form that is hygroscopic. Alternatively, aminopterin salts that are hermetically sealed from the atmosphere will not absorb moisture. In both instances, by avoiding moisture adsorption, the pharmaceutical compositions disclosed herein remain stable over time.

As used herein, 'aminopterin' means the free acid form, or N-4-[[2,4-diamino-6-pteridinyl)-methyl]amino]benzoy-1]-L-glutamic acid. Aminopterin may be prepared using the processes described in U.S. Pat. No. 7,235,660, hereby incorporated by reference in its entirety. It is noted that aminopterin may form a salt with various inorganic and organic acids and bases, which salts may be prepared by conventional methods. The disodium salt is preferred. Methods for determining if an aminopterin salt is hygroscopic will be familiar to those in the art, and include for example, Karl-Fischer titration (coulometric and volumetric), as well as elemental analysis.

In embodiments where the composition is intended to be exposed to the atmosphere, the aminopterin salt will typically comprise only a small percentage of the total pharmaceutical composition, with the balance comprising excipients. The amount of an aminopterin salt in the pharmaceutical composition is preferably from about 0.01 weight % (wt. %) to about 10 wt. %, based on the total weight of the pharmaceutical composition. More preferably, the amount of an aminopterin salt in the pharmaceutical composition is from about 0.1 wt. % to about 1 wt. %, most preferably about 0.25 wt. % and about 1.0 wt. %. In embodiments where the pharmaceutical composition is hermetically sealed from the atmosphere, the aminopterin salt may comprise any percentage of the total pharmaceutical composition, including 100%.

Preferably, the aminopterin salt is present in the pharmaceutical composition in an amount from about 0.01 mg to about 4 mg.

The stabilized pharmaceutical compositions of the disclosure thus also contain one or more excipients that are normally employed in pharmaceutical formulations, the only qualification being that they must not deleteriously affect the stability of the surface deposited aminopterin salt. Examples of such excipients are surfactants, diluents, binders, amino acids, solubilizers, disintegrants, fillers, lubricants, buffers, stabilizers, colorants, dyes, anti-oxidants, anti-adherents, preservatives and glidants. A combination of excipients may also be used. Such excipients are known to those skilled in the art, and thus in the interests of brevity, only a limited number will be specifically referenced.

Examples of fillers include microcrystalline cellulose, lactose, mannitol, starch, dibasic calcium phosphate dihydrate, calcium sulfate trihydrate and calcium sulfate dehydrate. A combination of fillers may also be used. A preferred filler is a combination of microcrystalline cellulose and lactose. Antioxidant fillers include monothioglycerol, L-cysteine and thioglycolic acid.

Examples of lubricants include magnesium stearate, sodium stearate, calcium stearate, zinc stearate, talc, propylene glycol, PEG, stearic acid, vegetable oil, sodium benzoate, sodium lauryl sulfate, magnesium lauryl sulfate, mineral oil and polyoxyethylene monostearate. A combination of lubricants may also be used. A preferred lubricant is magnesium stearate.

Examples of binders include gums, such as gum tragacanth, acacia gum and gelatin; microcrystalline cellulose, e.g., products known under the registered trademarks Avicel, Filtrak, Heweten or Pharmacel, hydroxyethyl cellulose, hydroxypropyl cellulose and hydroxypropylmethyl cellulose; and polyvinyl pyrrolidone, e.g., Povidone.

Examples of glidants include silica, magnesium trisilicate, powdered cellulose, talc, calcium silicate, and tribasic calcium phosphate. Colloidal silica, e.g., Aerosil, is particularly preferred.

Examples of disintegrants include cross-linked polyvinylpyrrolidones, e.g., crospovidones, such as Polyplasdone® XL and Kollidon® CL; alginic acid and sodium alginate; methacrylic acid-divinylbenzene co-polymer salts, e.g., Amberlite® IRP-88; and cross-linked sodium carboxymethylcellulose, available as, e.g., Ac-di-sol®, Primellose®, Pharmacel® XL, Explocel® and Nymcel® ZSX. Additional disintegrants also include hydroxypropylmethyl cellulose, croscarmellose sodium, polacrillin potassium, polyacrylates, such as Carbopol®, magnesium aluminium silicate and bentonite. Croscarmellose sodium is preferred.

The stable pharmaceutical compositions of the disclosure can be prepared by any of the conventionally employed processing techniques for a wet granulation process.

In one embodiment of the disclosure, the pharmaceutical composition is prepared by a process comprising: (a) mixing the aminopterin salt and one or more excipients, to form a premix; (b) adding a solvent, and optionally one or more excipients, to the premix formed in step (a) to form a wet granulation; (c) drying the wet granulation to form granules, and optionally milling the granules; and (d) optionally mixing one or more excipients with the granules to form a pharmaceutical composition.

In a preferred embodiment of the disclosure, the pharmaceutical composition is prepared by a process comprising: (a) mixing the aminopterin salt and a solvent, to form a solution; (b) adding the solution to one or more excipients to form a wet granulation; (c) drying the wet granulation to form granules, and optionally milling the granules; and (d) optionally mixing one or more excipients with the granules to form a pharmaceutical composition.

Examples of solvents to be used in the wet granulation process include water, methanol, dimethylformamide, ethylene glycol and tetrahydrofuran. A combination of solvents may also be used. Preferably, the solvent is water.

Drying techniques useful for drying the granulation include spray-drying, fluid bed, flash drying, ring drying, micron drying, tray drying, vacuum drying, radio-frequency drying and microwave drying. Preferred embodiments of drying to not expose the composition to excessive temperature for prolonged periods. Preferably the temperature does not exceed 30° C. The preferred method is drying in a fluid bed with unheated air, although tray drying without heating at room temperature is also useful.

The pharmaceutical compositions of the disclosure may be in the form of a capsule, caplet, powder, disc or tablet. In a preferred embodiment, the pharmaceutical composition in the form of a tablet obtained through compression of the pharmaceutical composition.

In embodiments where the pharmaceutical composition is hermetically sealed from the atmosphere, the pharmaceutical composition is preferably in a vial. Other packaging for hermetically sealing the pharmaceutical composition from the atmosphere will be known to those skilled in art.

With respect to sealing in a vial, it is generally preferred that the process for preparing the pharmaceutical composition includes the use of a purge of an inert gas. Such inert gases are, for example, nitrogen, argon, and the like. The use of an isolator to maintain low oxygen conditions is desirable, but not required for storage of the present pharmaceutical composition.

While any pharmaceutically acceptable stopper may be used to seal the vial containing the pharmaceutical composition, it is preferred to seal the vial with a stopper which is siliconized. A sterilized teflon coated stopper is desired for sealing the storage vial.

Most pharmaceutically acceptable liquid formulation vials or containers can be used to dispense the claimed pharmaceutical composition. It is desired that the containing vessel minimizes the concentration of ambient atmosphere that reaches the pharmaceutical composition. Thus, vials or ampules are especially desired vessels for the claimed pharmaceutical composition. A sealed vial is especially desired for commercial purposes in most countries.

The artisan will appreciate that the use of depyrogenated prewashed vials is desired for the storage of a sterile pharmaceutical composition that is intended for parenteral use. The vial may be colored, and an amber colored vial is preferred for storage. Any pharmaceutically acceptable material may be used to make the pharmaceutical composition container; however, glass is an especially preferred container material. A glass vial is a preferred container. Other packaging materials for parenterals like plastic vials are preferred options as well. For example, plastic vials may be useful.

Vials may be filled with solid pharmaceutical composition or bulk liquid pharmaceutical composition that is then desiccated. It is desirable to protect the bulk liquid from light during the process of preparing the sealed pharmaceutical composition.

The solid or bulk pharmaceutical composition can be sterilized using methods known to the artisan that do not involve excessive heating. Such sterilization methods may include, for example, sterile filtration of the bulk liquid prior to desiccation.

It is preferred that the headspace of the vial contains less than about 10% (ten percent) v/v ambient atmosphere with the balance an inert gas. It is more preferred that the headspace of the vial contains from about 2% to about 5% atmosphere.

The headspace of the vial can be adjusted to minimize contact of the pharmaceutical composition with atmosphere. It is generally desired that the headspace is not more than about 9/10 (nine tenths) of the total volume of the container, with the fill taking at least about 1/10 (one tenth) of the total volume of the container. For example, it may be preferred that 0.5 ml of fill be used for a 4.5 ml vial.

The pharmaceutical compositions provided herein are suitable for both human clinical use and veterinarian use for animals.

The following non-limiting examples illustrate further aspects of the disclosure.

Examples 1-5

The water content of aminopterin disodium was determined using Karl Fischer titration as a function of exposure time to the ambient atmosphere. Several glass scintillation vials and lids were dried in a >90° C. oven for 24 hrs, and their mass recorded with their lids. To each was added about 8 ml of methanol, then layered with argon, and the lids closed tightly. The mass of each was recorded with their lids. About 50 mg of aminopterin disodium was then added to each vial that had been exposed to the atmosphere for different durations. The vials were layered with argon, and closed tightly with a lid. The mass was again recorded. To a positive control vial was added 10 microliters (μl) of water. A negative control vial contained nothing except methanol. The mass of both controls were recorded.

TABLE 1

Hygroscopicity of aminopterin disodium

| Example | Exposure to atmosphere | Mole equivalents water to aminopterin |
|---|---|---|
| 1 | zero exposure, from vacuum | 1.5 |
| 2 | 1-2 hours exposure | 3.5 |
| 3 | 2-3 hours exposure | 4.5 |
| 4 | 5-6 hours exposure | 6.0 |
| 5 | 24 hour exposure | 11.0 |

The water content of each sample was measured by injecting two 500 μl aliquots of each into an Aquacounter AQ-300 coulometric titrator. The mass of water in the positive and negative controls were 10,266 μg and 322 μg, respectively. The mole equivalents of water to aminopterin in each aminopterin disodium sample are indicated in TABLE 1 as Examples 1-5.

Examples 6-10

The aqueous instability of aminopterin disodium was determined at a pH of 6.83, 9.29, 12.01 and 12.96 at room temperature (0.013 mg/ml with pH adjusted to the indicated values with NaOH). Degradation (loss of aminopterin) was monitored at 0, 0.5, 1, 2, 4, 8 and 24 hours using a two-solvent gradient high-pressure liquid chromatography (HPLC) system. The two solvents were 0.1 M triethylammonium acetate (TEAC, solvent A) and acetonitrile (solvent B). The HPLC was equipped with a 2.0 mm×50 mm column that contained packing L1 per USP <621> (e.g. Phenomenex Gemini 110 Å, 5 μm, C18). Mobile phase conditions were 95% solvent A: 5% solvent B to 5% solvent A: 95% solvent B over 30 minutes, hold at 95% solvent B for 10 minutes, and re-equilibrate at 95% solvent A: 5% solvent B for 15 minutes. The flow rate was 0.200 ml/min. Peak response was measured by light absorption at 260 nm using a variable wavelength detector. The approximate retention time of aminopterin was 7.1 to 7.2 minutes. The instability to water at various pH values is shown in TABLE 2 as Examples 6-9.

TABLE 2

Water instability of aminopterin salts

| Example | Salt | Concentration (mg/ml) | pH | Starting at t = 0 | Remaining at 24 hours | Remaining at year 5 |
|---|---|---|---|---|---|---|
| 6 | disodium | 0.013 | 6.83 | 98.1% | 96.1% | — |
| 7 | disodium | 0.013 | 9.29 | 98.1% | 96.6% | — |
| 8 | disodium | 0.013 | 12.01 | 98.8% | 97.3% | — |
| 9 | disodium | 0.013 | 12.96 | 99.8% | 86.8% | — |
| 10 | disodium | 2.0 | 8.0 | 100% | — | 93.5% |

A sterile liquid formulation of aminopterin for injection or oral administration was prepared with phosphate buffered saline (PBS) at pH 8.0. The stability of the liquid formulation was monitored over time using a 'radioligand binding assay' performed essentially as described previously [see Kamen et al., *Anal. Biochem.* 70:54, 1976 and Ratliff et al., *J. Clin. Onc.* 16:1458, 1998]. The instability to water is shown in TABLE 2 as Example 10.

Example 11

Preparation of aminopterin disodium 1 mg tablets: Surface deposited aminopterin disodium by combining 16.8 grams aminopterin (free acid), 791.0 grams microcrystalline cellulose, 553.7 grams lactose monohydrate, 1.5 g NaOH and 632 grams of sterile water. Mixed and dried overnight. Added 1311 grams of this surface deposited aminopterin to 171 grams of lactose, 3.9 grams colloidal silicon dioxide, 46.2 grams sodium croscarmellose, and 7.7 grams magnesium stearate that provided a total weight 1540 grams. Compressed into approximately 15,000 tablets using a tableting machine, wherein each tablet weighs approximately 100 mg and contains about 1 mg aminopterin disodium, 52.1 mg microcrystalline cellulose, 42.93 mg lactose, 3.00 mg sodium croscarmellose, 0.50 mg magnesium stearate, and 0.25 colloidal silicon dioxide.

Example 12

Preparation of hermetically sealed aminopterin disodium: Clean glassware to be used with 2 M NaOH for 3-5 minutes and the rinse thoroughly with deionized water. Prepare a first saline buffer by adding 2.7017 grams of dibasic sodium phosphate, USP to 5 liters of 0.9% sodium chloride for injection, USP. Prepare a second saline buffer by adding 1.39 grams of monobasic sodium phosphate, USP to 1 liter of 0.9% sodium chloride for injection, USP. While stirring the first saline buffer solution, slowly add the second saline buffer solution until the final pH is 7.9-8.1. Record the final volume. Add sufficient aminopterin salt, preferably the disodium salt, to provide 0.4 mg/ml aminopterin (i.e. 2 mg aminopterin per 5 ml) and filter through a 0.2 micron membrane filter, desiccate by freeze drying to a solid powder, and package under sterile conditions in 10-ml vials that are sealed from the atmosphere. Resuspend with the appropriate amount of sterile water at the time of administration.

Example 13

The stability (i.e. amount of aminopterin remaining by assay) of the surface deposited aminopterin disodium tablets from EXAMPLE 11 was monitored over nearly 60 months using the radioligand binding assay and HPLC. The results are shown in TABLE 3 and demonstrate that formation of degradation products has been reduced or eliminated in the surface deposited pharmaceutical composition, resulting in long-term stability on storage under ambient conditions (15-30° C.). For the purposes herein, "stable" or "stability" shall mean no more than 3% degradation over a time period of greater than 1 year under normal climatic storage conditions.

TABLE 3

Stability of surface deposited aminopterin disodium 1 mg tablets

| Date of Testing | Age (months) | HPLC assay | Radioligand assay |
|---|---|---|---|
| June 2001 | 5 | — | 98.6% |
| October 2001 | 9 | — | 99.6% |
| June 2002 | 17 | — | 98.4% |
| October 2002 | 21 | — | 99.0% |
| June 2003 | 29 | — | 98.1% |
| October 2003 | 33 | — | 100.7% |
| June 2004 | 41 | — | 98.4% |
| October 2004 | 45 | — | 98.1% |
| June 2005 | 53 | 97.8% | 98.0% |

While the disclosure has been described with particular reference to certain embodiments thereof, it will be understood that changes and modifications may be made by those of ordinary skill within the scope and spirit of the following claims:

What is claimed is:

1. A stable pharmaceutical composition of aminopterin disodium salt, wherein the composition comprises a plurality of granules having a solid body and a surface, wherein the solid body consists of microcrystalline cellulose and lactose monohydrate, and wherein the surface of the solid body consists of aminopterin disodium salt, and an excipient comprising lactose, silicon dioxide, sodium croscarmellose, magnesium stearate, and no aminopterin disodium salt, wherein the granules are coated by the excipient, and wherein the aminopterin disodium salt comprises 0.01 to 10 weight percent of the composition.

2. The stable pharmaceutical composition of claim 1, wherein the aminopterin salt is from about 0.1 weight percent to about 1 weight percent of the composition.

3. The stable pharmaceutical composition of claim 1, wherein the aminopterin disodium salt is from about 0.25 weight percent to about 1 weight percent of the composition.

4. The stable pharmaceutical composition of claim 1, wherein the composition is in a form of a capsule, caplet, powder, disc, or tablet.

5. A method for preparing a stable pharmaceutical composition of an aminopterin salt, comprising:

(a) mixing a solution consisting of an aminopterin salt and a solvent;

(b) adding the solution of step (a) to a solid body consisting of microcrystalline cellulose and lactose monohydrate to form a wet granulation; and (c) drying the wet granulation to form granules.

6. The method for preparing a stable pharmaceutical composition of claim 5, further comprising mixing one or more additional excipients with the dried granules to form a pharmaceutical composition.

7. The method for preparing a stable pharmaceutical composition of claim 5, wherein the solvent is water.

8. The method for preparing a stable pharmaceutical composition of claim 5, wherein step (c) is performed in a fluid bed dryer.

9. The method for preparing a stable pharmaceutical composition of claim 6, further comprising the step of compressing the pharmaceutical composition into a tablet.

10. The stable pharmaceutical composition of claim 4, wherein the total amount of aminopterin disodium salt in the capsule, caplet, disc, or tablet is from 0.01 mg to 4 mg.

11. The stable pharmaceutical composition of claim 1, wherein the composition is in a form of a tablet.

12. The stable pharmaceutical composition of claim 1, wherein the composition is prepared by (a) mixing the aminopterin salt and a solvent, to form a solution;

(b) adding the solution of step (a) to the solid bodies to form a wet granulation; and (c) drying the wet granulation to form dried granules.

13. The stable pharmaceutical composition of claim 12, wherein the dried granules are mixed with one or more additional excipients.

* * * * *